(12) United States Patent
Carpenter et al.

(10) Patent No.: US 10,130,664 B2
(45) Date of Patent: *Nov. 20, 2018

(54) COMPOSITIONS AND METHODS FOR DECREASING THE EFFECTS OF ALCOHOL

(71) Applicant: BiOWiSH Technologies, Inc., Cincinnati, OH (US)

(72) Inventors: Richard Carpenter, West Chester, OH (US); Amit Kapur, East Corrimal (AU); E. Wesley Huff, Pleasant Grove, UT (US); Narayan Suresh, Brookfield, WI (US)

(73) Assignee: BiOWiSH Technologies, Inc., Cincinnati, OH (US)

( * ) Notice: Subject to any disclaimer, the term of this patent is extended or adjusted under 35 U.S.C. 154(b) by 922 days.

This patent is subject to a terminal disclaimer.

(21) Appl. No.: 14/275,683

(22) Filed: May 12, 2014

(65) Prior Publication Data
US 2014/0335187 A1 Nov. 13, 2014

Related U.S. Application Data

(60) Provisional application No. 61/821,974, filed on May 10, 2013.

(51) Int. Cl.
| | |
|---|---|
| *A61K 35/66* | (2015.01) |
| *A61K 35/74* | (2015.01) |
| *A61K 35/747* | (2015.01) |
| *A61K 9/14* | (2006.01) |
| *A61K 35/744* | (2015.01) |
| *A61K 9/20* | (2006.01) |
| *A61K 9/19* | (2006.01) |

(52) U.S. Cl.
CPC ............. *A61K 35/747* (2013.01); *A61K 9/14* (2013.01); *A61K 9/19* (2013.01); *A61K 9/20* (2013.01); *A61K 35/744* (2013.01)

(58) Field of Classification Search
None
See application file for complete search history.

(56) References Cited

U.S. PATENT DOCUMENTS

| | | | |
|---|---|---|---|
| 2003/0235559 A1* | 12/2003 | Sobol | A23C 9/133 424/93.4 |
| 2006/0233774 A1 | 10/2006 | Lim et al. | |
| 2006/0263385 A1 | 11/2006 | Gare | |
| 2009/0169530 A1 | 7/2009 | Tsuda et al. | |
| 2011/0236358 A1 | 9/2011 | Sala | |

FOREIGN PATENT DOCUMENTS

| | | |
|---|---|---|
| CN | 102934809 A | 2/2013 |
| FR | 2 881 751 A1 | 8/2006 |
| JP | A 2009-184998 | 8/2009 |
| WO | WO 1998/07867 A2 | 2/1998 |
| WO | WO 2012/170915 A1 | 12/2012 |
| WO | WO 2014/022279 A1 | 2/2014 |
| WO | WO 2014/067976 A1 | 5/2014 |

OTHER PUBLICATIONS

Kirpich et al., "Probiotics restore bowel flora and improve liver enzymes in human alcohol-induced liver injury: a pilot study", Alcohol, Pergamon Press, London, GB, vol. 42, No. 8, Dec. 1, 2008, pp. 675-682.
Reid, M. F., "Molecular Characterization of Microbial Alcohol Dehydrogenases" Critical Reviews in Microbiology, CRC Press, Inc., Boca Raton, FL, US, vol. 20, No. 1, Jan. 1, 1994, pp. 13-56.
Pasteris S.E. et al., "Aerobic glycerol catabolism by Pediococcus pentosaceus isolated from wine", Food Microbiology, Academic Press Ltd., London, GB, vol. 22, No. 5, Oct. 1, 2005, pp. 399-407.
International Search Report issued for application No. PCT/US2014/037704, dated Sep. 29, 2014.

\* cited by examiner

*Primary Examiner* — Christopher R Tate
*Assistant Examiner* — Douglas F White
(74) *Attorney, Agent, or Firm* — Cooley LLP; Ivor R. Elrifi; Cynthia A. Kozakiewicz

(57) ABSTRACT

The present invention relates probiotic compositions useful in accelerating alcohol catabolism in a subject.

20 Claims, 2 Drawing Sheets

COMPOSITIONS AND METHODS FOR DECREASING THE EFFECTS OF ALCOHOL

RELATED APPLICATIONS

This application claims priority to and benefit of provisional application U.S. Ser. No. 61/821,974 filed on May 10, 2013, the contents of which are herein incorporated by reference in its entirety.

FIELD OF THE INVENTION

The present invention relates to compositions containing probiotic bacteria and their use in alleviating one or more adverse effects associated with alcohol toxicity.

BACKGROUND OF THE INVENTION

Probiotics are microbial organisms that are associated with beneficial health effects and may be used for the prevention and treatment of diseases. When administered exogenously, probiotics can survive in sufficient numbers to affect gut microbial metabolism.

Alcohol is absorbed mainly in the digestive tract, and 90% of the absorbed alcohol is metabolized in the liver while the remaining 10% is discharged via expiration, urine and perspiration. Alcohol, after being transported along with blood, is oxidized to acetaldehyde by various liver enzymes, such as alcohol dehydrogenase, a microsomal ethanol oxidizing system, catalase, etc., which is further enzymatically oxidized to acetic acid, which is harmless to the body. Meanwhile, alcohol is readily metabolized to acetaldehyde by enteric microorganisms. Recently, lactic acid bacteria in the intestine have been reported to convert ethanol into acetaldehyde and further to acetic acid, thereby suppressing the absorption of alcohol and acetaldehyde, with the concomitant hepatoprotective activity. However, not all enteric bacteria have such a function. Therefore, there is a need for developing the bacterial compositions that functions to prevent the absorption of alcohol and acetaldehyde and protect the liver.

SUMMARY OF THE INVENTION

In various aspects the invention provides a composition of a mixture of bacteria containing *Pediococcus acidilactici, Pediococcus pentosaceus* and *Lactobacillus plantarum*. Each of the bacteria in the mixture is individually anaerobically fermented, harvested, dried, and ground to produce a powder having a mean particle size of 295 microns, with 60% of the mixture in the size range between 175-840 microns. The mixture has a moisture content of less than about 5%; and a final bacterial concentration of about between $10^5$-$10^{11}$ colony forming units (CFU) per gram of the composition.

In some aspects, the bacteria are anaerobically fermented in the presence of carbohydrates. Carbohydrates include for example inulin, fructo-oligosaccharide, and gluco-oligosaccharides. The bacteria are harvested by any method known in the art, such as by filtration or centrifugation. The bacteria are dried by known methods. For example, the bacteria are dried by liquid nitrogen followed by lyophilization. The bacteria are ground by conical grinding at a temperature less than 4° C.

Also included in the invention are formulations containing the bacterial composition of the invention and a vitamin, a mineral or a sugar. Vitamins include for example, Vitamin D, Vitamin B12, Vitamin C or Vitamin E. Sugars include for example is inulin, dextrose or fructose. Minerals include for example, calcium, magnesium, sodium, potassium, zinc, copper, or molybdenum.

In some aspects the mixture of bacteria in the formulation is at a concentration of less than about 60.0% (w/w).

Also included in the invention are tablets, capsules and powders containing the bacteria mixtures and formulations according to the invention. The tablet contains about 687 mg of the bacterial composition. The total weight of the tablet is 1200 mg. The capsule or powder contains about at least 300 mg of the bacterial composition.

The invention further provides methods of increasing the rate of alcohol metabolism in a subject by administering to the subject the composition or formulations of the invention. The composition or formulation is administered orally. The composition or formulation is administered as a tablet, capsule, or powder. Each tablet, capsule, or powder contains between about 100-800 milligrams of the bacterial mixture. In some aspects, two tablets or capsules are administered before the consumption of alcohol. In other embodiments, 2 and 20 tablets or capsules are administered within a 24 hour period after the consumption of alcohol.

The invention further includes methods of manufacturing a composition of a mixture of bacteria containing *Pediococcus acidilactici, Pediococcus pentosaceus* and *Lactobacillus plantarum* by windividually anaerobically fermenting each organism; harvesting each organism; freezing the harvested organisms with liquid nitrogen, drying the frozen organisms; and grinding the dried organisms to produce a powder having a mean particle size of 295 microns, with 60% of the mixture in the size range between 175-840 microns. In some aspects, the methods further includes combining each of the individually fermented bacteria to produce a mixture of bacteria wherein the mixture has a moisture content of less than about 5%; and a final bacterial concentration of between about $10^5$-$10^{11}$ colony forming units (CFU) per gram of the composition.

In some aspects the bacteria are anaerobically fermented in the presence of carbohydrates. Carbohydrates include for example inulin, fructo-oligosaccharide, and gluco-oligosaccharides.

The bacteria are harvested by any method known in the art such as by filtration or centrifugation. The bacteria are dried by know methods. For example, the bacteria are dried by liquid nitrogen followed by lyophilization. The bacteria are ground by conical grinding at a temperature less than 4° C.

In some aspects the powder is granulated prior to tableting. The granulate comprises hydroxypropyl methy cellulose, water, hydroxylated soy lecithin, gellum gum, corn starch, dextrose, rice bran extracts, silica, or gum arabic. The granulate has a mean particle size range between 100 and 300 microns.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1:
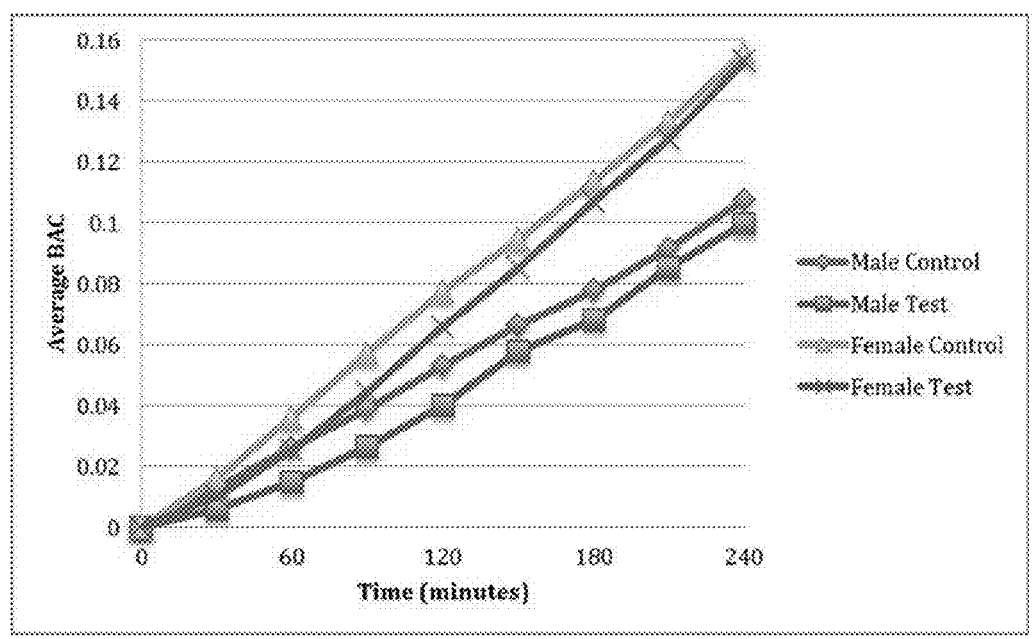
FIG. 1 is a line graph showing average BAC values of 10 male and 10 female participants in the treatment arm of the study. Average BAC is shown in the y-axis and time (minutes) is shown in the x-axis.

The invention provides probiotic compositions that are useful in reducing blood alcohol levels. The composition contains a mixture of *Pediococcus acidilactici, Pediococcus pentosaceus* and *Lactobacillus plantarum*.

The term "probiotic bacteria" or "probiotics" as used herein, refers to microorganisms which when administered in adequate amounts confer a health benefit to the consumer. The probiotics according to the invention may be viable or non-viable. In case the probiotics are non-viable, they have to be substantially structurally intact, meaning that these non-viable micro-organisms are still sufficiently intact to avoid or delay disintegration in the distal intestinal tract thereby enabling the interaction of (conserved structures of) the non-viable micro-organisms with the immune system, particularly the mucosal immune system, The non-viable probiotics are metabolically-active. By "metabolically-active" is meant that they exhibit at least some residual enzyme activity characteristic to that type of probiotic.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of replication under suitable growing conditions in a population which is otherwise defined as non-viable.

By the term "viable bacteria" as used herein is meant a population of bacteria that is capable of replicating under suitable conditions under which replication is possible. A population of bacteria that does not fulfill the definition of "non-viable" (as given above) is considered to be "viable".

By the term "bioactive, component" as used herein is meant a component which has a physiological effect upon the body when consumed in adequate amounts.

Unless stated otherwise, all percentages mentioned in this document are by weight based on the total weight of the composition.

The probiotic bacteria used in the product according to the present invention may be any conventional probiotic bacteria. The probiotic bacteria is food grade. It is preferred that the probiotic bacteria are selected from the family Lactobacillacea.

Suitable types of probiotic bacteria which may be used include *Pediococcus acidilactici, Pediococcus pentosaceus* and *Lactobacillus plantarum*.

In preferred compositions, the probiotic bacteria *Pediococcus acidilactici, Pedococcus pentosaceus* and *Lactobacillus plantarum* are present in equal proportions.

The levels of the probiotic bacteria to be used according the present invention will depend upon the types thereof. It is preferred that the present product contains probiotic bacteria in an amount between $10^5$ and $10^{11}$ colony forming units per gram.

In some embodiments of the invention, the probiotic bacteria employed are viable probiotic bacteria. The use of viable probiotic bacteria offers the advantage that these probiotic bacteria may become a part of the intestinal microflora, thereby providing additional health benefits.

The probiotic bacteria according to the invention may be produced using any standard fermentation process known in the art. For example, solid substrate or submerged liquid fermentation. The fermented cultures can be mixed cultures or single isolates. The probiotic bacteria are anaerobically fermented.

In some embodiments the probiotic bacteria are anaerobically fermented in the presence of carbohydrates. Suitable carbohydrates include inulin, fructo-oligosaccharide, and gluco-oligosaccharides.

After fermentation the bacteria are harvested by any known methods in the art. For example the bacteria are harvested by filtration or centrifugation.

The bacteria are dried by any method known in the art. For example the bacteria are dried by liquid nitrogen followed by lyophilization.

The compositions according to the invention have been freeze dried to moisture content less than 20%, 15%, 10% 9%, 8%, 7%, 6%, 5%, 4%, 3%, 2%, or 1%. Preferably, the composition according to the invention has been freeze dried to moisture content less than 5%.

In some embodiments the freeze dried powder is ground to decrease the particle size. The bacteria are ground by conical grinding at a temperature less than 10° C., 9° C., 8° C., 7° C., 6° C., 5° C., 4° C., 3° C., 1° C., 0° C., or less. Preferably the temperature is less than 4° C.

For example the particle size is less than 1500, 1400, 1300, 1200, 1100, 1000, 900, 800, 700, 600, or 500 microns. Preferably, the freeze dried powder is ground to decrease the particle size such that the particle size is less than 800 microns. Most preferred are particle sizes less than about 400 microns. in most preferred embodiments the freeze dried powder has a mean particle size of 295 microns, with 60% of the mixture in the size range between 175-840 microns. In various embodiments the freeze dried powder is homogenized.

Naturally, the present composition may contain further ingredients, including ingredients that have a favorable health impact. Non-limiting examples of additional ingredients that may suitably be incorporated in the present composition are: vitamins, minerals, prebiotics, phytosterols, polyphenols, proteins, fibers, herbs and saponins.

The compositions of the invention are formulated for oral administrations, including chewable foods, beverages, liquids, tablets, capsules, powders, and granulates. In a preferred embodiment the probiotic compositions have been formulated into a tablet. In another preferred embodiment the probiotic compositions have been formulated into a capsule. In yet another preferred embodiment the probiotic compositions have been formulated into a granulate or a water soluble powder.

When formulated the composition may contain further ingredients, including ingredients that have a favorable impact on flavor or tableting. Non-limiting examples of additional ingredients that may suitably be incorporated in the present composition are: calcium lactate, sugars, tableting aids and flavorings.

When formulated for oral administration the compositions comprises at least 5, 10, 15, 20, 25, 30, 35, 40, 45, 50, 55 or more w/w % of the mixture of probiotic bacteria. Preferably, the composition comprises between about 50 to 60 w/w % probiotic bacteria.

In preferred embodiments the probiotic compositions of the invention are formulated in to a tablet and comprise minerals, vitamins, sugars, tableting aids and flavoring.

Minerals include for example Calcium Carbonate, Calcium Lactate, Calcium Chloride, Calcium Phosphate (dibasic), Sodium Chloride, Potassium Citrate monohydrate, Potassium sulfate, Potassium Phosphate monobasic, Magnesium Oxide, Manganese Carbonate, manganese glucanate, Ferric Citrate, Zinc Carbonate, Zinc glucanate, Cupric Carbonate, Potassium Iodate, Sodium Selenite pentahydrate, Chromium potassium sulfate dodecahydrate, Ammonium paramolybdate tetrahydrate, Sodium meta-silicate nonahydrate, lithium chloride, boric acid, sodium fluoride Nickel Carbonate hydroxide tetrahydrate, or ammonium meta-vanadate. Minerals are formulated at a concentration of about 0.1% to 10%, w/w, 0.1% to 5.0% w/w or any specific value within said range. In specific embodiments, minerals are formulated at a concentration of about 5% w/w, 4%, 3% w/w, 2% w/w, 1% w/w, 0.9% w/w, 0.8% w/w, 0.7% w/w, 0.6% w/w, 0.5% w/w, 0.4% w/w, 0.3% w/w, 0.2% w/w, 0.1% w/w or less.

Vitamins include fbr example, Vitamin B1, B2, B3, B5, B6, B7, B9, B12, Vitamin C, Vitamin D, or Vitamin E. Preferred vitamins are Vitamin B1, B3, B6 B12, Vitamin C, Vitamin D3, or Vitamin E acetate. Vitamins are formulated at a concentration of about 0.01% to 10%, w/w, 0.1% and 5 w/w %, or any specific value within said range. In particular vitamins are formulated at a concentration of about 5% w/w, 4%, 3% w/w, 2% w/w, 1% w/w, 0.9% w/w, 0.8% w/w, 0.7% w/w, 0.6% w/w, 0.5% w/w, 0.4% w/w, 0.3% w/w, 0.2% w/w, 0.1% w/w or less.

Sugars include for example, dextrose, sucrose, fructose, inulin, trehalose or salts of gluconic acid. Preferred sugars include dextrose, fructose, facto-oligosaccharides, gluco-oligosaccharides or sucralose. Sugars are formulated at a concentration of about 10% to 50%, w/w, 20%-40% w/w, or any specific value within said range. In particular vitamins are formulated at a concentration of about 50% w/w, 45% w/w, 40%, 35% w/w, 30% w/w, 25% w/w, 20% w/w, 15% w/w, 10% w/w, or less.

Tableting aids include for example, polycarboxylic acids such as malic, maleic, citric, iso-citric and succinic, and salts thereof, $SiO_2$, Aloe Vera, saturated and unsaturated linear and branched fatty acids and their salts, or fatty alcohols. Preferred tableting aides are malic acid, citric acid, stearic acid or Magnesium stearate. Tableting aides are formulated at a concentration of about 1% to 10%, w/w, 2.5% and 7.5 w/w % or any specific value within said range. In particular vitamins are formulated at a concentration of about 10% w/w, 7.5%. 5% w/w, 4%, 3% w/w, 2% w/w, 1% w/w, or less.

Any natural or artificial food grade flavorings maybe used including Banana, Cinnamon, Grape, Orange, Peach, Pear Pineapple, Apple, Berry, Coconut, Chocolate, Vanilla, Strawberry, Wintergreen, Spearmint, Peppermint or Ginger. Preferred flavorings are ginger or natural berry flavorings. Flavorings are formulated at a concentration of about 0.1% to 10%, w/w, 0.5% and 5 w/w % or any specific value within said range. In particular flavoring agenets are formulated at a concentration of about 5% w/w, 4%, 3% w/w, 2% w/w, 1% w/w, 0.9% w/w, 0.8% w/w, 0.7% w/w, 0.6% w/w, 0.5% w/w, 0.4% w/w, 0.3% w/w, 0.2% w/w, 0.1% w/w or less.

In a particularly preferred embodiment the probiotic compositions of the invention are formulated in to a tablet and comprise 58.0% w/w mixed probiotic bacteria; 0.58% w/w calcium lactate, 2.95% w/w vitamins, 2.11% w/w minerals, 31.70% w/w sugars, 2.66% w/w tableting aids and 2.00% flavoring.

The invention also includes tablets, capsules or powders containing the bacterial compositions according to the invention.

The tablet contains about 1000 mg, 900 mg, 800 mg, 700 mg, 600 mg, 500 mg or less of the bacterial composition. In one embodiment the tablet contains 687 mg of the bacterial composition. The total weight or the tablet is 1500 mg, 1400 mg, 1300 mg, 1200 mg, 1100 mg, 1000 mg, 750 mg, or 500 mg.

The capsule contains 1000 mg, 900 mg, 800 mg, 700 mg, 600 mg, 500 mg, 400 mg, 300 mg or 200 mg the bacterial composition.

The powder contains 1000 mg, 900 mg, 800 mg, 700 mg, 600 mg, 500 mg, 400 mg, 300 mg or 200 mg the bacterial composition.

In a further aspect the invention provides a method of increasing the rate of alcohol metabolism, reducing blood alcohol levels or alleviating one or more adverse effects associated with alcohol toxicity by orally administering to a subject the probiotic bacterial compositions according to the invention. The composition is preferably administered prior to, during or after the consumption of alcohol. Alternatively, the composition is administered prior to the consumption of alcohol and every hour thereafter until the subject ceases to consume alcohol. In some embodiments 2 to 20 tablets or capsules are administered within a 24 hour period after consumption of alcohol.

The initial doses contain about 0.5-5 grams of probiotic bacteria. Preferably, the initial dose contains about 1.5-3.5 grams of probiotic bacteria. Most preferably, the initial dose contains about 2.75 grams of probiotic bacteria. In some aspects the subsequent doses contain half of the initial dose.

Also included in the invention are methods of manufacturing a composition of a mixture of bacteria containing *Pediococcus acidilactici, Pediococcus pentosaceus* and *Lactobacillus plantarum*. The method includes individually anaerobically fermenting each organism; harvesting each organism; freezing the harvested organisms with liquid nitrogen drying the frozen organisms; and grinding the dried organisms to produce a powder having a mean particle size of 295 microns, with 60% of the mixture in the size range between 175-840 microns.

In some embodiments the method further includes, combining each of the individually fermented bacteria to produce a mixture of bacteria wherein the mixture has ta moisture content of less than about 5%; and a final bacterial concentration of between about $10^5$-$10^{11}$ colony forming units (CFU) per gram of the composition.

A better understanding of the present invention may be given with the following examples which are set forth to illustrate, but are not to be construed to limit the present invention.

EXAMPLES

Example 1

Preparation of the Microbial Species

The microbial mixture of the present invention may be made by any of the standard fermentation processes known in the art. In the following examples, both solid state and submerged liquid fermentation processes are described:

A. Solid State Fermentation

Individual purified isolates of *Pediococcus acidilactici, Pediococcus pentosaceus* and *Lactobacillus plantarum* were grown-up in separate fermenters using standard anaerobic submerged liquid fermentation protocols. The individual organisms were recovered from the fermenters via centrifugation, mixed together in equal proportions on a weight basis, then added to the following mixture: 1 part inulin, 2.2 parts isolated soy protein, 8 parts rice flour with 0.25% w/w sodium chloride, 0.045% w/w Calcium carbonate, 0.025% w/w Magnesium sulphate, 0.025% w/w Sodium phosphate, 0.012% w/w Ferrous sulphate and 29.6% water. This mixture was allowed to ferment for up to 5 days at 30° C. Upon completion of the fermentation, the entire mixture was freeze dried to a moisture content less than 5%, ground to an average particle size of 295 microns, with 60% of the product in the size range between 175-840 microns, and homogenized. The final microbial concentration of the powdered product is between $10^9$ and $10^{11}$ CFU/g.

B. Submerged Liquid Fermentation

Individual, purified isolates of *Pediococcus acidilactici*, *Pediococcus pentosaceus* and *Lactobacillus plantarum* were grown-up in separate fermenters using standard anaerobic submerged liquid fermentation protocols. After fermentation the individual cultures were filtered, centrifuged, freeze dried to a moisture level less than about 5%, then ground to a mean particle size of 295 microns, with 60% of the product in a size range between 175-840 microns. The individual dried microbial cultures were then mixed in equal proportion by weight to obtain the microbial composition of the present invention. The final microbial concentration of the mixed powdered product is between $10^9$ and $10^{11}$ CFU/g.

Example 2

Tablet Formulation

The dried microbial mixture from Example 1 was formulated into tablets for clinical studies. The tablets had the following composition:

| Ingredient | % w/w |
| --- | --- |
| Dried, mixed microbial culture from Example 1 | 58.0% |
| Calcium Lactate | 0.58% |
| Vitamin D3 100 IU | 0.01% |
| Vitamin E 950 acetate | 2.63% |
| Vitamin C | 0.29% |
| Vitamin B12 | 0.02% |
| Citric Acid | 0.70% |
| Malic Acid | 0.58% |
| Sugars | 31.70% |
| Mineral Mix (Zn, Mn, Mg) | 0.83% |
| Tableting Aids | 2.66% |
| Flavoring | 2.00% |

Final Tablet Characteristics:

| | |
| --- | --- |
| Appearance | Off white to medium brown |
| Dimensions | 0.555 × 0.555 in$^2$ |
| Avg. Tablet Wt. | 1.2 grams |
| Hardness | 32-38 kp |
| Friability | <=2% loss |

Example 3

Performance of the Tableted Product in Mitigating the Effects of Alcohol

A small-base (20-person) clinical study was conducted to evaluate the tablet composition of Example 2 for its ability to accelerate alcohol metabolism. Recruited human subjects were between 21-40 years old with a Body Mass Index of 18.5-24.9. Subjects with allergies or intolerance to any of the ingredients in the study, including alcohol used (e.g. sulphites), were excluded.

The study ran for 2-days with 20 healthy non-smoking male and female volunteers. Subjects were grouped by gender (10 per test leg). Subjects took an initial oral dose of 4.8 grams of the composition from Example 2 then drank a glass of wine (100 mls). One hour later, and every hour thereafter during the course of the test, subjects ingested another 2.4 grams of the composition from Example 2. Alcohol was consumed every 30 minutes for the duration of the study (240 minutes in total). Breathalyzer tests (BAC) were administered at baseline (before the first dose or first glass of alcohol) and every 20 minutes after consumption of each dose of alcohol:

Study Protocol

| Time (minutes) | Drink (100 mL 12% alcohol by volume) Participants consume drink in 5 minutes | Amount of Test Composition from Example 2 |
| --- | --- | --- |
| 0 | 1 | 4.8 g |
| 30 | 2 | |
| 60 | 3 | 2.4 g |
| 90 | 4 | |
| 120 | 5 | 2.4 g |
| 150 | 6 | |
| 180 | 7 | 2.4 g |
| 210 | 8 | |
| 240 | 9 | |

There were no adverse effects that could be attributed to ingestion of the composition of Example 2. In almost all cases, participants reported a marked reduction in the adverse effects normally associated with alcoholic toxicity. There was a marked reduction in BAC response among participants who ingested the composition of Example 2 versus a control group (FIG. 1).

Example 4

Comparison to Competitive Product

Figure 2:
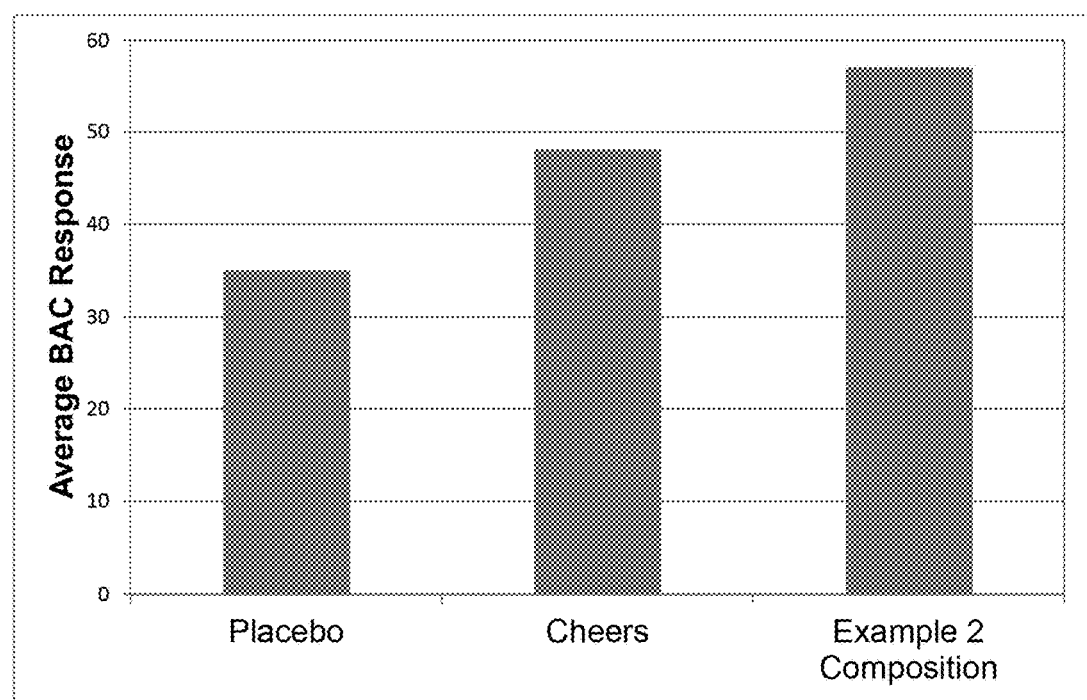
FIG. 2 is a bar chart showing the BAC response after ingestion of microbial composition and alcohol.

A repeat clinical study, similar in design to that in Example 3 above, was conducted to compare the performance of the composition of Example 2 to a competitive product (Cheers, Juventa Technologies). Results are shown in FIG. 2. These results confirm that the microbial composition of the present invention is preferred for reducing the effects of alcohol consumption.

We claim:

1. A method of increasing the rate of alcohol metabolism in a subject in need thereof, comprising administering to the subject an effective amount of a composition comprising a mixture of bacteria comprising *Pediococcus acidilactici*, *Pediococcus pentosaceus* and *Lactobacillus plantarum*, wherein each of the bacteria in the mixture is individually anaerobically fermented, harvested, dried, and ground to produce a powder having a mean particle size of 295 microns, with 60% of the mixture in the size range between 175-840 microns, and the mixture has the following characteristics:

a) a moisture content of less than about 5%; and b) a final bacterial concentration of about between $10^5$-$10^{11}$ colony forming units (CFU) per gram of the composition.

2. The method of claim 1, wherein the bacteria are harvested by filtration or centrifugation.

3. The method of claim 1, wherein the bacteria are dried by liquid nitrogen followed by lyophilization.

4. The method of claim 1, wherein the bacteria are ground by conical grinding at a temperature less than 4° C.

5. The method of claim 1, wherein the mixture of bacteria is at a concentration of less than about 60.0% (w/w) in the composition.

6. The method of claim 1, wherein the composition is administered orally.

7. The method of claim 6, wherein the composition is administered as a tablet, capsule, or powder.

8. The method of claim 7, wherein each tablet, capsule, or powder contains between about 100-800 milligrams of the mixture of bacteria.

9. The method of claim 7, wherein the capsule comprises at least 300 mg of the composition.

10. The method of claim 7, wherein the powder comprises at least 300 mg of the composition.

11. The method of claim 7, wherein two tablets or capsules are administered before the consumption of alcohol.

12. The method of claim 11, further comprising administering between 2 and 20 tablets or capsule within a 24 hour period after the consumption of alcohol.

13. The method of claim 7, wherein the tablet comprises 687 mg of the composition.

14. The method of claim 13, wherein the total weight of the tablet is 1200 mg.

15. The method of claim 1, wherein the bacteria are anaerobically fermented in the presence of carbohydrates.

16. The method of claim 15, wherein the carbohydrates are selected from the group consisting of inulin, fructo-oligosaccharides, and gluco-oligosaccharides.

17. The method of claim 1, wherein the composition further comprises a vitamin, a mineral or a sugar.

18. The method of claim 17, wherein the vitamin is Vitamin D, Vitamin B12, Vitamin C or Vitamin E.

19. The method of claim 17, wherein the sugar is inulin, dextrose or fructose.

20. The method of claim 17, wherein the mineral is calcium, magnesium, sodium, potassium, zinc, copper, or molybdenum.

* * * * *